United States Patent [19]

Franke

[11] Patent Number: 6,166,087

[45] Date of Patent: Dec. 26, 2000

[54] LOW DOSED 15-DEOXYSPERGUALIN PREPARATIONS

[76] Inventor: Niels Franke, Nymphenburger Strasse 90e, D-80636 München, Germany

[21] Appl. No.: 09/446,896

[22] PCT Filed: Jun. 26, 1998

[86] PCT No.: PCT/EP98/03927

§ 371 Date: May 4, 2000

§ 102(e) Date: May 4, 2000

[87] PCT Pub. No.: WO99/01123

PCT Pub. Date: Jan. 14, 1999

[30] Foreign Application Priority Data

Jul. 3, 1997 [DE] Germany .................. 197 28 436

[51] Int. Cl.⁷ .................................................. A61K 31/155
[52] U.S. Cl. .............................................................. 514/634
[58] Field of Search ............................................ 514/634

[56] References Cited

FOREIGN PATENT DOCUMENTS

| | | |
|---|---|---|
| 0 600 762 | 6/1994 | European Pat. Off. . |
| 44 17 816 | 11/1995 | Germany . |
| 92 02229 | 2/1992 | WIPO . |
| 96 24579 | 8/1995 | WIPO . |
| 96 00058 | 1/1996 | WIPO . |

OTHER PUBLICATIONS

Database WPI, Derwent Publications Ltd. AN 90–056185 & JP 02 011514.

*Primary Examiner*—James H. Reamer
*Attorney, Agent, or Firm*—Arent Fox Kintner; Plotkin & Kahn, PLLC

[57] ABSTRACT

15-deoxyspergualin or a pharmaceutically compatible salt thereof is suitable for the preparation of an immunosuppressive, anti-inflammatory or anti-tumoral pharmaceutical, which is effective in a low dosage of 20 to 600 $\mu$g/kg body weight when it is applied to the mucous membrane, to which end it is preferably prepared as a dosing aerosol.

11 Claims, No Drawings

LOW DOSED 15-DEOXYSPERGUALIN PREPARATIONS

This application is a 371 of PCT/EP98/03927 filed Jun. 26, 1998.

DESCRIPTION

The present invention concerns the use of 15-deoxyspergualin for the production of an immunosuppressive, anti-inflammatory and anti-tumoral pharmaceutical for administration to the mucous membrane in a dosage in the range from 20 to 600 μm/kg body weight per day, especially for treating autoimmune illnesses, inflammatory skin disorders, cancer diseases and for the prevention of transplant rejection. The active substance (±) 15-deoxyspergualin with the formula $$H_2NC(=NH)NH(CH_2)_8CONHCH(OH)CONH(CH_2)_4NH(CH_2)_3NH_2(3HCl)$$

is a synthetic derivative of the anti-tumoral antibiotic spergualin.

The compound can be prepared either as a racemic mixture (cf, for example, U.S. Pat. No. 4,518,532) or else in optically pure form (cf., for example, EP-A-0 094 632).

Although numerous publications describe the immunosuppressive properties of this compound and its potential suitability for treating autoimmune illnesses, such as multiple sclerosis, lupus erythematosus and for preventing transplant rejection, its clinical benefit is very limited on account of the very high doses required and the associated side effects.

The main side effect observed in long-term therapy was a temporary drop in leucocyte count with all the consequences of a strong immunosuppression (cf. Amemiya, H,. et al.: Japanese [Journal] of Transplantation, 26, 615). The high dosages were regarded as necessary because of these demonstrable immunosuppressive effects in the therapy of acute and chronic rejection as well as in the treatment of autoimmune illnesses (cf. Amemiya., et al.: Transplantation Proceedings XXIII, (1), 1087–1089, February 1991).

Conventionally, 15-deoxyspergualin is administered intravenously in a dosage of approx. 4 to 6 μg/kg of body weight to obtain an immunosuppressive effect. The effect is characterized by a non-specific general suppression of the immune system.

For treatment of autoimmune illnesses and cancer diseases and for the prevention of transplant rejection, at present no satisfactory long-term treatments with low side effects are available. The object of the invention is therefore to make available a preparation for the treatment of the aforementioned illnesses, which has low side effects, is easy to administer, does not develop significant side effects even during long-term use and is therapeutically effective. Furthermore, the preparation should be easy to administer even by the patient himself.

Surprisingly, it has now been found that extremely small dosages (20 to 600 micrograms/kg body mass) are sufficient to obtain the desired immunosuppressive pharmacological effects if the active substance is applied by way of the respiratory mucous membranes. The risk of undesired effects is considerably reduced, The ordeal of daily injection is eliminated. However, the low-dosage therapy presupposes that precise dosage systems are used in order to ensure the necessary constancy of dosage of highly effective immunosuppressants. In the dosage according to the invention, the active ingredient DSG can be administered by means of the preferred dosing aerosol precisely in the microgram range to the nasal mucous membrane, the respiratory tracts or other mucous membranes, the individual dosage being determined by the amount of active substance per stroke (200 to 800 microgram per stroke). Because of the low and, at the same time, precise dosage in the microgram range, it is possible for the first time to realize in practice the pharmacological effects that can be obtained in this dosage. In the process, both local and systemic effects are produced, since a sufficient amount of the active substance is resorbed and passes into the bloodstream. For long-term therapy, transdermal systems are also suitable in the low-dosage range.

The object of the invention is the use of 15-deoxyspergualin or a pharmaceutically compatible salt thereof as active substance, if appropriate with the conventional auxiliary and carrier substances and/or other active substances for the preparation of an immunosuppressive anti-inflammatory or anti-tumoral pharmaceutical in the form of a preparation intended for application to the mucous membrane in a dosage of 20 to 600 μg/kg body weight per day, preferably in the form of a dosing aerosol.

Since the immunosuppressive anti-inflammatory and anti-tumoral effect at this low dosage is very selective, only slight, if any, side effects, such as, for example, dysaesthesias, are to be expected, even in long-term therapy.

As a result, autoimmune illnesses, certain cancer diseases and transplant rejection reactions can be treated with low side effects. According to the invention, autoimmune illnesses of any origin and any organ can be treated, for example myasthenia gravis, myositis, multiple sclerosis, Hashimoto's thyroiditis, athropic gastritis, colitis ulcerosa, nephrotoxic nephritis, lupus illnesses, arthritis, scleroderma, granulomatosis, autoimmune hepatitis, endo- and myocarditis, autoimmune cytopenia, psoriasis, neurodermatitis, dermatitis herpetiformis, eczema, morbus basedow, pancreatitis, uveitis, iritis, glomerulonephritis, rheumatoid arthritis, Alzheimer's disease, AIDS and the like. The treatment of multiple sclerosis, lupus erythematosus, virus-induced autoimmune diseases, AIDS, glomerulonephritis, psoriasis and neurodermatitis is preferred. The cancer diseases that can be treated include leukaemia and solid tumours, for example, of the lung, breast, sarcoma, ovaries, lymphoma. Transplant rejection reactions may occur in the transplantation of any human organ or tissue. The fate of the transplant depends essentially on the nature and extent of the immune reaction in the recipient. As a result of the immune suppression caused by the pharmaceutical obtained in accordance with the invention, the survival time of the transplant is considerably improved.

Hitherto, the active substance deoxyspergualin could only be administered intravenously or intramuscularly on account of the high doses required. The invention, by contrast, allows the active substance to be administered effectively in the low dosage required in accordance with the invention by mucous-membrane application.

The essential dosage within the scope of the invention is in the range from 20 to 600 μg/kg body weight per day. It is preferably reliably maintained therein that the pharmaceutical in accordance with the invention is packaged and used in a dosing aerosol applicator, which, with each actuation, administers a specified amount of active substance. If, for example, the dosing aerosol device is arranged such that, with each stroke, aerosol with a content of 500 μg of active substance is sprayed out, then, for a patient of 60 kg body weight and a dosage of 100 μg/kg body weight per day; this results in 6 pump actions to each side of the nose, corresponding to 2 pump actions per side of the nose 3× per day. The daily dose is suitably administered distributed between one to three individual doses.

The dosage to be administered in a particular case will be decided by the doctor, taking into account the severity of the condition to be treated, the patient's age, sex and weight, and the duration of the treatment.

Although the pharmaceutical to be produced according to the invention is preferably formulated as an aerosol, it can also, for example, be in the form of an ointment, a cream, drops, or a lotion, which is formulated for application to the mucous membrane, preferably to the nasal mucous membrane.

Administration to the nasal mucous membrane or respiratory mucous membrane, for example, in the form of a nasal spray, aerosol, nasal ointment or nasal drops is preferred, since the ordeal for the patient is thereby considerably reduced and the patient's compliance can thus also be improved. As a result of the low dosage of the active substance, such nasal administration is possible for the first time, since, by virtue of the low concentrations, no irritation of the mucous membrane occurs. There is also no effect on the ciliar function. Also appropriate is buccal administration, in which the active substance can be resorbed via the oral mucous membrane. Dosed administration of the pharmaceutical in accordance with the invention is also possible via the vaginal mucous membrane and the intestinal mucous membrane, in which case the formulation then assumes the conventional preparation form for this application, for example as a suppository.

The active substance deoxyspergualin can be packaged for use in accordance with the invention in a manner known per se and processed for a galenic form of application. To this end auxiliary materials and carriers conventional in the field of pharmaceutical formulations for the particular form of administration are used.

The active substance can either be used as a free base or as a pharmaceutically compatible acid addition salt together with conventional carriers and other conventional pharmaceutical additives are used. Examples of pharmaceutically compatible acid addition salts with organic and inorganic acids include, for example, chlorides, hydroxides, lactates, malates, fumarates, acetates, carbonates, citrates, tartrates, glycolates, etc.

15-Deoxyspergualin can either be used as a single active substance or else together with other active substances as well as vitamins, minerals and known pharmaceutical additives. Examples of suitable further active substances are those with a pharmacological effect, in so far as they are compatible with 15-deoxyspergualin, for example corticosteroids such as cortisone, camphor, echinacea, euphorbium etc. or active substances with a complementary accompanying effect, such as fumaric acid, active substances promoting the absorption and penetration of 15-deoxyspergualin, such as 2-propanol or propylene glycol, active substances with a soothing effect, such as camomile oil, Azulene, panthenol, retinol palmitate and glycerine.

For the production of a preparation to be administered preferably to the respiratory or nasal mucous membrane, all auxiliary and carrier substances conventionally used in the field of mucous membrane agents can be used. The preparation, except for the preferred embodiment as dosing aerosol, can also take any other form appropriate for the precisely dosable administration via the mucous membrane, and may exist, for example, in the form of a nasal spray, nasal drops, nasal ointment, nasal suspension, nasal gel or the like. To this end base materials adapted to the form of administration may be used, such as medium-chain triglycerides, peanut oil, Carbomer, Makrogol, wool wax, alcohol salbene base, water for injection, paraffin liquidum and excipients such as preservatives, for example benzalkonium chloride, thiomersal, butylhydroxytoluene, PHB ester, isotonic agents, such as sodium dihydrogenphosphate or sodium chloride, and flavouring and aromatizing substances, such as fennel oil, eucalyptus oil, peppermint oil, dwarf pine-needle oil, cedar-leaf oil, and the like can be used. The nasal spray may take the form of a pump spray or be embodied in a pressure vessel with a pharmacologically acceptable propellant gas. Particularly preferred is the packaging in a dosing aerosol container.

The combination of deoxyspergualin with magnesium is particularly preferred. It was found that the compatibility of this combination is particularly high. Magnesium reliably prevents the (rarely) occurring subjective complaints (for example, dysaesthesias) during treatment with 15-deoxyspergualin.

The invention is described in greater detail below with reference to the examples.

EXAMPLES

Example 1

Nasal Spray

By mixing 2.5 mg and 5 mg respectively of pulverized 15-deoxyspergualin with 100 g of a carrier substance, e.g. glucose in purified water, a nasal spray is prepared in a manner known per se. Application is as directed by the doctor.

Example 2

Nasal Drops

By mixing 2.5 mg, 5 mg and 10 mg respectively of powdered 15-deoxyspergualin with 100 ml of a liquid carrier medium, e.g. glycol, and conventional auxiliaries, nasal drops are prepared in a manner known per se. Dosage is as directed by the doctor.

Example 3

Ointment 10 mg of 15-deoxyspergualin and 50 g of Eucerin are processed with conventional auxiliaries and additives and processed to prepare an ointment. The ointment is applied to the mucous membrane several times per day.

Example 4

Ointment 10 mg of 15-deoxyspergualin are processed with 50 g of purified Vaseline, ethereal oils and Azulene in a manner known per se. The ointment is applied to the mucous membrane several times per day.

Example 5

Ointment 10 mg of 15-deoxyspergualin is processed with 50 g of Eucerin and 1.0 g of fumaric acid, if appropriate with the addition of fragrances and conservation agents, to prepare an ointment. The ointment is applied to the mucous membrane several times per day.

Example 6

Nasal Oil 250 mg of deoxyspergualin are processed with paraffinum liquidum, benzalkonium chloride and sodium citrate in a manner known per se to prepare 10 ml of nasal oil. The nasal oil is introduced into the nose according to the dosage directions of the doctor.

Example 7

Nasal Drops 20 mg of deoxyspergualin are processed with 2 mmol of magnesium chloride and 100 ml of purified water, if appropriate with the addition of camomile flower fluid extract, in a manner known per se. Dosage is carried out as directed by the doctor.

Example 8

Dosing Aerosol 50 mg of deoxyspergualin are processed with ethyl acetate, sorbitol trioleate, dichlorodifluoromethane and trichlorofluoromethane to form a dosing aerosol comprising 200 individual doses. Dosage is carried out as directed by the doctor.

Example 9

Treatment of Multiple Sclerosis Relapsing Form (EDSS<5).

Patient 1: female, 31 years, 60 kg body weight, MS diagnosis 1989 by clinic, magnetic resonance imaging and evidence of oligoclonal banding in cerebrospinal fluid, so far approximately 2 relapses per year, slowly progressive incapacity, presentation August 1994, walking range approx. 100 m with stick, slight paraspastis, dynaesthesias, pensioned 12 months ago.

Therapy was carried out with 150 µg/kg body weight of 15-deoxyspergualin as aerosol, applied to the nasal mucous membrane over 14 days. On further presentation after 6 weeks, the walking range was now approx. half an hour. There were no more dysaesthesias and paraspastis. The gait was normal. Further therapy with 15-deoxyspergualin over 14 days led to a normal condition which has remained unchanged since. Since June 1997 working again, no new relapses. Neither subjective nor objective side effects of the therapy were observed.

Patient 2: male, 25 years, 81 kg body weight, MS diagnosis 1992 by clinic, magnetic resonance imaging and evidence of oligoclonal banding in cerebrospinal fluid, so far approximately 4 relapses per year, slowly progressive incapacity, presentation July 1995, walking range approx. 50 m, ataxis, ataxic-spastic gait, intense tiredness.

A nasal-aerosol therapy with 150 µg/kg body weight of 15-deoxyspergualin over 14 days produced a significant improvement at the next presentation after 7 weeks. The tiredness had disappeared, the walking range had increased to about 5 km and the gait had normalized. A further 14-day therapy with 150 µg/kg body weight per day 15-deoxyspergualin produced a further improvement. No further relapses occurred. Overall, normal mobility is now present. Neither subjective nor objective side effects of the therapy were observed.

Example 10

Treatment of Multiple Sclerosis, Primary Chronic Progressive Form

Patient 1: male, 29 years, 65 kg, MS diagnosis in 1991 by clinic, magnetic resonance imaging and oligoclonal banding in cerebrospinal fluid, presentation March 1996, walking range approx. 100 m, spastic—ataxic gait, disturbed fine motor skill, intense tiredness, incapable of working (student).

A 16-day aerosol therapy with 100 µg/kg body weight of 15-deoxyspergualin per day brought about a significant improvement. The tiredness had disappeared, the walking range had increased to about 500 m, the fine motor skill was normal again and the gait had visibly improved. The patient felt able to meet his demands again. Further therapy with 15-deoxyspergualin over 16 days brought about a further stabilization of the general condition, and the patient felt further capable of meeting his demands. Neither subjective nor objective side effects of the therapy were observed.

Patient 2: Female, 41 years, 57 kg, MS diagnosis in 1987 by clinic, magnetic resonance imaging and oligoclonal banding in cerebrospinal fluid, presentation May 1996, chronic tiredness, walking range 150 m, spastic-ataxic gait, significantly reduced strength in hands, slight ataxia of hands.

After therapy with 100 µg/kg body weight of 15-deoxyspergualin for 18 days by infusion, at the next presentation after 6 weeks, the walking range had increased to approx. 200 m, the gait was more regular, the strength of the hands was increased, the fine motor skill was better. Further therapy with 7.5 mg of 15-deoxyspergualin over 18 days as nasal spray stabilized the condition further, so that the patient felt capable of doing her housework again.

Example 11

Treatment of Lupus Erythematosus a. Lupus Erythematosus (LE), Cutaneous Forn

Patient: male, 12 years, 40 kg, diagnosis in 1995 by skin biopsy and clinic, presentation in July 1996, numerous skin spots and lesions on the entire body, previous therapy 40 mg Decortin/day, chronic tiredness.

Therapy with 50 µg/kg 15-deoxyspergualin over 20 days by aerosol brought a clear improvement at the further presentation 6 weeks later. The skin lesions and tiredness had disappeared and Decortin could be discontinued . A further 20 days' therapy with 2 mg 15-deoxyspergualin per day by nasal spray brought about a stabilization of the condition. Side effects of the therapy were not observed.

b. Lupus Erythematosus (LE), Systemic LE (SLE)

Patient: male, 16 years, 42 kg, diagnosis in 1989 by clinic and laboratory tests, presentation in July 1994, nephrotic syndrome with high protein loss (7.5 g/l) from the kidney, butterfly erythem in face, chronic tiredness, school attendance not possible for two years.

A therapy with 250 µg/kg 15-deoxyspergualin per day for 14 days by aerosol brought about a clear improvement in the condition of the illness at the next presentation 5 weeks later. The patient was able to attend school again, the tiredness had disappeared, the protein excretion through the kidney (2.9 g/l) was significantly reduced, the butterfly erythem had faded. A further therapy with 0.25 mg/kg body weight of 15-deoxyspergualin over 16 days by infusion brought about a further improvement. There was no more protein excretion through the kidney, the patient's condition was stable, regular school attendance was possible.

Example 12

Treatment of Glomerulonephritis

Patient: male, 29 years, 74 kg, diagnosis in 1995 by kidney biopsis, chronic tiredness, presentation November 1995, tiredness, elevated creatinine (1.9 mg), liquid retention.

Therapy with 150 µg/kg body weight of 15-deoxyspergualin over 18 days by aerosol brought about a clearly improved condition of the illness at a further presentation after 6 weeks. The creatinine content in the serum was reduced (1.3 mg). A further therapy with 150 µg/kg body weight of 15-deoxyspergualin over 18 days by infusion brought about a further normalization of the creatinine level (0.7 mg). The kidney biopsy brought about a clear reduction in the symptoms of glomerulonephritis. Neither subjective nor objective side effects of the therapy were observed.

Example 13

Treatment of Rheumatoid Arthritis (ra)

Patient: male, 36 years, 79 kg, diagnosis in 1987 by clinic and positive rheumafactor, presentation in June 1996, chronic tiredness, painful limited movement in the finger, knee and shoulder joints.

A therapy with 200 µg/kg body weight of 15-deoxyspergualin over 18 days by aerosol brought about a dear improvement in the condition of the illness at a further presentation after 6 weeks. The tiredness had disappeared. The movement in the joints had improved, as had the pains. A further therapy with 7.5 mg 15-deoxyspergualin per day by a nasal spray over 20 days brought about a further stabilization of the condition of the illness. No further relapses in the illness occurred, the rheumafactor was negative. Neither subjective nor objective side effects of the therapy were observed.

Example 14

Treatment of an HIV Infection

Patient: male, 29 years, 72 kg, with confirmed HIV infection and depressed suppressor cell count (<750) no symptoms of AIDS, presentation in April 1995, chronic tiredness.

A therapy with 7.5 mg 15-deoxyspergualin per day, administered via a nasal spray, for five times 18 days improved the tiredness and led to an increase in CD8 cells to a count of over 900. Neither subjective nor objective side effects were observed.

Example 15

Treatment of Neurodermatitis

Patient: male, 10 years, 22 kg with neurodermatitis, diagnosis 1990, presentation August 1995, painful itching patches on skin on the trunk and extremities, improvement with cortisone ointment.

Therapy with grease-free 15-DSG emulsion (10 mg/10 g emulsion) applied to the nasal mucous membrane over 20 days. After two repetitions at intervals of 6 weeks, healing of the skin patches without complications, no occurrence of new itching patches. Neither subjective nor objective side effects were observed.

Example 16

Treatment of Myasthenia Gravis

Patient: female, 39 years, 62 kg, diagnosis in 1983 by clinic and serology, therapy with 150 µg/kg body weight of 15-deoxyspergualin aerosol for two times 14 days. A lasting neurological improvement with an absence of further relapses occurred. Neither subjective nor objective side effects were observed.

Example 17

Treatment of Leukaemia

Patient: male, 19 years, ALL, diagnosis in 1995 by clinic, diagnosis 1995 confirmed by clinic, blood picture, immunohistochemistry and blood marrow biopsy, presentation May 1996.

Therapy with 50 µg/kg body weight of 15-deoxyspergualin for 25 days and further therapy with 5 mg 15-deoxyspergualin by nasal spray brought about a complete remission after 8 weeks until now. Neither subjective nor objective side effects were observed.

What is claimed is:

1. Use of 15-deoxyspergualin or a pharmaceutically compatible salt thereof as active substance, if appropriate together with conventional auxiliary and carrier substances and/or further active substances for the preparation of an immunosuppressive anti-inflammatory or anti-tumoral pharmaceutical in the form of a preparation intended for application to the mucous membrane in a dosage of 20 to 600 µg/kg body weight per day.

2. Use according to claim 1,
    characterized in that
        said pharmaceutical is prepared as a dosing aerosol.

3. Method according to claim 1,
    characterized in that
        application is to the mucous membrane of the nose or the respiratory tracts.

4. Use according to claim 1 for the treatment of autoimmune illnesses, cancer diseases or transplant rejection reactions.

5. Use according to claim 4 for the treatment of multiple sclerosis, myasthenia gravis, lupus erythematosus, virus-induced autoimmune illnesses, AIDS, glomerulonephritis or psoriasis, neurodermatitis, eczema.

6. Use according to claim 1
    characterized in that
        the pharmaceutical additionally contains magnesium and/or a corticosteroid.

7. Use according to claim 1 for the preparation of a pharmaceutical as dosing aerosol.

8. Method for obtaining immunosuppression by application of a deoxyspergualin or a pharmaceutically compatible salt thereof as active substance-containing aerosol in a dosage of 20 to 600 µg/kg body weight per day to the mucous membrane.

9. Method according to claim 8,
    characterized in that
        an autoimmune illness, inflammatory illness, cancer disease or transplant rejection reaction is treated.

10. Method according to claim 9,
    characterized in that
        multiple sclerosis, lupus erythematosus, a virus-induced autoimmune illness, AIDS, glomerulonephritis or psoriasis, neurodermatitis, eczema, myasthenia gravis is treated.

11. Dosing aerosol device,
characterized in that
it contains a pharmaceutical with 15-deoxyspergualin or a pharmaceutically compatible salt thereof as active substance, if appropriate together with conventional auxiliaries and carriers and/or further active substances for the preparation of an immunosuppressive anti-inflammatory or anti-tumoral pharmaceutical which is formulated for application to the mucous membrane and contains the active substance in a concentration such that an amount of 20 to 600 µg/kg body weight per day is dispensed in the aerosol during conventional use of device.

* * * * *